United States Patent [19]

Berger et al.

[11] 4,071,531
[45] Jan. 31, 1978

[54] OXATHIINO- AND DITHIINO-AMINOACETIC ACIDS

[75] Inventors: Christian Berger, Le Plessis Robinson; Daniel Farge, Thiais; Georges Gros, Bourg-la-Reine; Mayer Naoum Messer, Bievres; Claude Moutonnier, Le Plessis-Robinson, all of France

[73] Assignee: Rhone-Poulenc Industries, Paris, France

[21] Appl. No.: 616,991

[22] Filed: Sept. 26, 1975

[30] Foreign Application Priority Data

Sept. 27, 1974 France .................................. 74 32702

[51] Int. Cl.$^2$ .................. C07D 501/60; C07D 327/06; C07D 339/08; A61K 31/54
[52] U.S. Cl. ................................ 260/327 P; 560/153; 544/28; 424/246
[58] Field of Search ............. 260/327 P, 239.1, 243 C

[56]     References Cited
       U.S. PATENT DOCUMENTS 3,928,595   12/1975   Dahlen et al. .................... 424/271
3,966,718   6/1976    Brain et al. ..................... 260/243 C

*Primary Examiner*—Cecilia M. S. Jaisle

*Attorney, Agent, or Firm*—Stevens, Davis, Miller & Mosher

[57]         ABSTRACT

New oxathiino- and dithiino-aminoacetic acids of the formula:

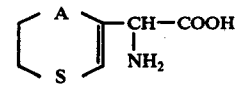

in which A represents oxygen or sulphur, together with their racemic forms, their optically active forms and mixtures thereof, their reactive derivatives and their acid addition salts, are valuable intermediates for the preparation of therapeutically active derivatives, in particular cephalosporin derivatives of the formula:

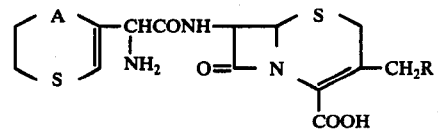

where R is hydrogen or acetoxy.

5 Claims, No Drawings

OXATHIINO- AND DITHIINO-AMINOACETIC ACIDS

The present invention relates to new oxathiino dithiino-aminoacetic acids and to their preparation.

The present invention provides oxathiino- and dithiino-aminoacetic acids of formula:

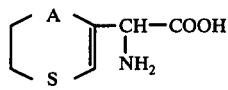 (I)

in which A represents oxygen or sulphur, together with their racemic forms, their optically active forms and mixtures thereof, and their acid addition salts and reactive derivatives.

The acids of formula (I) can be obtained according to another aspect of this invention by saponifying an ester of formula:

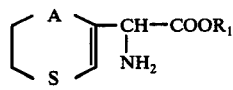 (II)

in which A is defined as above, and $R_1$ represents alkyl of 1 to 4 carbon atoms, in manner known per se for saponifying an ester to the corresponding acid.

In general, the ester of formula (II) is treated with an alkali metal hydroxide in an aqueous-alcoholic medium and at a temperature of between 0° and 50° C. Preferably, the methyl ester or ethyl ester is used and the saponification is carried out in an aqueous-methanolic medium at a temperature of about 5° C.

The ester of formula (II) can be obtained by reduction of an oxime of formula:

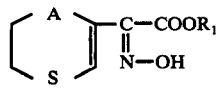 (III)

in which A and $R_1$ are as defined above.

In general, the reduction is carried out using zinc in an aqueous-organic medium such as a mixture of methanol, formic acid and water, at a temperature of between 0° and 25° C.

The oxime of formula (III) can be obtained by reaction of a compound of formula:

$$HA - CH_2CH_2 - SH \quad (IV)$$

in which A is as defined above, with an ester of formula:

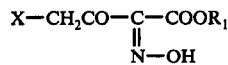 (V)

in which $R_1$ is as defined above and X represents halogen, preferably chlorine. The reaction takes place via an intermediate product of formula:

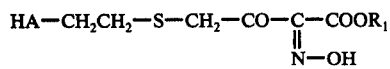 (VI)

in which A and $R_1$ are as defined above, which is subsequently cyclised.

The reaction of the compound of formula (IV) with the ester of formula (V) is generally carried out in an organic solvent such as chloroform in the presence of an acid acceptor such as triethylamine, preferably at a temperature of about 20° C.

The cyclisation of the ester of formula (VI) to give the oxime of formula (III) is generally carried out by heating the ester of formula (VI) in an organic solvent, such as benzene or toluene, in the presence of a dehydrating catalyst such as p-toluenesulphonic acid, and removing the water at the rate at which it is formed.

The optically active forms of the acid of formula (I) can be obtained either by chemical methods or by enzymatic methods. For example, the D-form of the acid of formula (I) can be obtained by treating the racemic form with (+) - camphorsulphonic acid in an organic solvent such as an alcohol, for example methanol or ethanol to give the salt of the D-form, purifying this salt by recrystallisation and liberating the free acid from this salt. The L-form of the acid of formula (I) can be obtained, for example, by selective enzymatic desacetylation of an acid of formula:

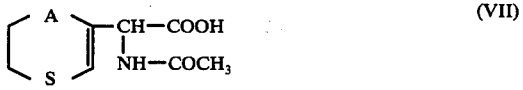 (VII)

in which A is as defined above.

The treatment of the racemic form of the acid of formula (VII) with an amino-acylase gives the L-form of the acid of formula (I) and the D-form of the acid of formula (VII).

Preferably, the selective desacetylation is carried out by an Aspergillus amino-acylase, at a pH of about 8 and a temperature of about 37° C.

The acid of formula (VII) can be obtained according to one of the following processes:

a. By acetylation of the acid of formula (I), for example with acetyl chloride or acetic anhydride, or b. by saponification or hydrolysis of the corresponding ester, preferably, the corresponding methyl or ethyl ester.

The methyl or ethyl ester of the acid of formula (VII) can be obtained by reaction of a compound of formula (IV) with an ester of formula:

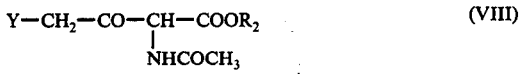 (VIII)

in which Y represents halogen, preferably bromine, and $R_2$ represents methyl or ethyl, the reaction taking place via an intermediate product of formula:

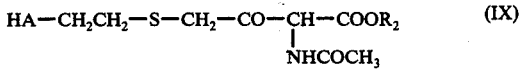 (IX)

in which A and $R_2$ are as defined above, which is subsequently cyclised.

In general, the reaction of the compound of formula (IV) with the ester of formula (VIII) is carried out in an organic solvent such as chloroform, in the presence of an acid acceptor such as triethylamine, at a temperature of about 20° C.

The cyclisation of the product of formula (IX) to give an ester of the acid of formula (VII) is generally carried out by heating the product of formula (IX) in an organic solvent such as benzene or toluene in the presence of a dehydrating catalyst such as p-toluenesulphonic acid, and removing the water at the rate at which it is formed.

The ester of formula (VIII) can be obtained according to the method of M. Hatanaka and T. Ishimaru, J. Med. Chem., 16, 978 (1973).

The acids of formula (I) can be purified by physical methods such as crystallisation or chromatography, or chemical methods such as conversion to a salt and reconversion to the free acid.

The compounds of formula (I) can be converted into their corresponding acid addition salts. These salts can be obtained by reacting the compounds of the formula (I) with an acid in an appropriate solvent. Examples of suitable organic solvents are alcohols, ethers or chlorinated solvents. The salt formed precipitates, if necessary after concentration of its solution, and is separated off by filtration or decantation.

The acids of formula (I) are advantageously employed as intermediates for the preparation of new therapeutically active derivatives. More particularly, the acids of formula (I) can be employed as starting materials for the preparation of cephalosporin derivatives of formula:

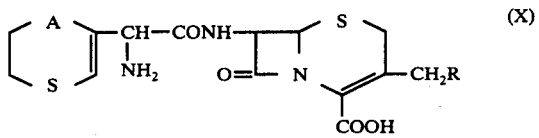

in which A is as defined above and R represents hydrogen or acetoxy; the said products, which are described and claimed in our copending application Ser. No. 617,066 filed Sept. 26, 1975, now U.S. Pat. No. 4,029,781 can exist in optically active forms derived from the D-, L- and DL forms of the compounds of formula (I).

The new cephalosporins of formula (X) can be obtained by reaction of an acid of formula (I), in its racemic or optically active form, and in which the amino group has been protected, or of a reactive derivative of this acid, such as an acid halide, anhydride or mixed anhydride, with a cephalosporin of formula:

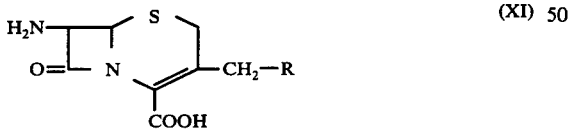

in which R is as defined above.

a. If an acid of formula (I) is used, the amino group is protected by any conventional method for blocking an amino group which does not affect the remainder of the molecule. It is necessary to protect the amino group by an easily removable group, such as tertiary butoxycarbonyl, which can be introduced by reaction of, for example, tertiary butyl azidoformate, tertiary butyl chloroformate or a mixed tertiary butyl/p-nitrophenyl carbonate with the acid of formula (I).

In general, the acid of formula (I), in which the amino group has been protected, is condensed with the cephalosporin derivative of formula (XI) in which the acid group has been protected by an easily removable group such as tertiary butyl or 2,2,2-trichloroethyl.

In general, the condensation is carried out in an organic solvent such as dimethylformamide or chloroform, in the presence of a condensation agent such as dicyclo-hexylcarbodiimide, at a temperature of between 0° and 40° C, and the groups which protect the amino and acid groups are then removed. This removal depends on the nature of the protecting groups, and may be effected in a single stage or in two stages. If the removal is carried out in two stages, it is preferable first to remove the group which protects the acid group and then the group which protects the amino group.

If the group which protects the amino group is tertiary butoxycarbonyl and the group which protects the acid group is tertiary butyl, their replacement by a hydrogen atom can be carried out in a single stage by treatment in an acid medium. Preferably, trifluoroacetic acid is used and the reaction is carried out at a temperature of about 20° C. Under these conditions, the cephalosporin of formula (X) is obtained in the form of a trifluoroacetate, from which the amino group may be liberated by any conventional method for obtaining an amine from one of its salts without affecting the remainder of the molecule.

If the group which protects the amino group is tertiary butoxycarbonyl and the group which protects the acid group is 2,2,2-trichloroethyl, the latter is first of all replaced by a hydrogen atom by treatment with zinc in acetic acid, and thereafter the tertiary butoxycarbonyl radical is replaced by a hydrogen atom by treatment in an acid medium, preferably by reaction with trifluoroacetic acid. Under these conditions, the cephalosporin of formula (X) is obtained in the form of a trifluoroacetate and the free amine can be obtained under the conditions described above.

b. If the acid of formula (I) is used in the form of a reactive derivative, it is particularly advantageous to employ its acid halide, especially the acid chloride. Under these conditions, the hydrochloride of the acid chloride of formula (I) is reacted with a cephalosporin derivative of formula (XI), in which the acid group need not be protected.

In general, the condensation is carried out in an organic solvent such as chloroform in the presence of an acid acceptor such as an organic nitrogen-containing base, for example pyridine or triethylamine, or in an aqueous-organic medium in the presence of an alkaline condensation agent such as sodium bicarbonate.

The cephalosporin of formula (XI) in which R represents hydrogen is 7-amino-3-desacetoxy-cephalosporanic acid (or 7-ADCA) which can be obtained, either from a penicillin in accordance with the process described in Belgian Patent Specification No. 747,382, or by desacetoxylation of a cephalosporin of formula (XI) in which R represents acetoxy, in accordance with the process described in Belgian Patent Specification No. 779,035.

The cephalosporin of formula (XI) in which R represents acetoxy is 7-amino-cephalosporanic acid (or 7-ACA), which can be obtained in accordance with the process described in Belgian Patent Specification No. 615,955 or in U.S. Pat. No. 3,239,394.

The cephalosporin derivatives of formula (X) can optionally be purified by physical methods such as crystallisation or chromatography. They can also be converted into metal salts or addition salts with nitrogen-containing bases in accordance with known methods.

The cephalosporin derivatives of formula (X) and their salts have particularly valuable anti-bacterial properties. They exhibit a remarkable activity in vitro and in vivo against Gram-positive and Gram-negative bacteria.

In vitro, the cephalosporin derivatives of formula (X) have proved active at concentrations of between 1 and 25 μg/cm³ against strains of staphylococci sensitive to penicillin G (*Staphylococcus aureus* 209 P and *Staphylococcus aureus* Smith) or at concentrations of between 1 and 50 μg/cm³ against strains of staphylococci which are resistant to penicillin G (*Staphylococcus aureus* MB 9) or, at concentrations of between 1 and 100 μg/cm³, against the Monod strain of *Escherichia coli*.

In vivo, the products have proved active against experimental infections of mice with *Staphylococcus aureus* Smith (sensitive to penicillin G) at doses of between 0.1 and 5 mg/kg per day given subcutaneously or between 0.1 and 30 mg/kg per day given orally, or with *Escherichia coli*, at doses of between 1 and 50 mg/kg per day given subcutaneously or of between 10 and 500 mg/kg per day given orally.

The following Examples further illustrate the present invention. Percentages are by weight.

EXAMPLE 1

Normal sodium hydroxide solution (820 cc.) is added to a solution of ethyl-DL-α-amino-(5,6-dihydro-1,4-dithiin-2-yl)-acetate (150 g.) in methanol (1,500 cc.). The reaction mixture is left for 16 hours at a temperature of about 5° C and then concentrated to dryness under reduced pressure (20 mm Hg). Water (500 cc.) is added to the resulting residue and the mixture is filtered through "Supercel". The yellow filtrate obtained is cooled in an ice bath and acidified by adding 4 N hydrochloric acid (600 cc.).

The acid solution is treated with decolourising charcoal, filtered and then brought to pH 4.5 by adding concentrated sodium hydroxide solution. The precipitate which has appeared is filtered off. DL-α-Amino-(5,6-dihydro-1,4-dithin-2-yl)-acetic acid (99 g. is thus obtained in the form of white crystals melting at about 260° C, with decomposition.

Ethyl DL-α-amino-(5,6-dihydro-1,4-dithiin-2-yl)-acetate can be prepared as follows:

50% Formic acid (1,600 cc.) is added to a solution of ethyl α-hydroxyimino-(5,6-dihydro-1,4-dithiin-2-yl)-acetate (171 g.) in methanol (800 cc.). The mixture is cooled to 5° C., and zinc powder (135 g.) is added in small portions in such a way that the temperature does not exceed 28° C. The mixture is then left stirring at 5° C., for 30 minutes, after which it is filtered, and the filtrate is concentrated under reduced pressure (20 mm.Hg) to a volume of about 1,000 cc. This residue is washed with methylene chloride (twice 200 cc.), water (1,500 cc.) is added to the aqueous phase and the latter is neutralised by adding sodium carbonate, until the pH is 8.9, in the presence of methylene chloride (500 cc.). The organic phase is separated off, the aqueous phase is washed with methylene chloride (500 cc.) and the organic extracts are combined, treated with decolourising charcoal and filtered. After concentration to dryness under reduced pressure (20 mm.Hg), ethyl DL-α-amino-(5,6-dihydro-1,4-dithiin-2-yl)-acetate (150 g.) is obtained in the form of a pale yellow oil.

Ethyl α-hydroxyimino-(5,6-dihydro-1,4-dithiin-2-yl)-acetate can be prepared as follows:

Ethyl 2-hydroxyimino-4-(2-mercapto-ethylthio)-3-oxo-butyrate (655 g.) is suspended in toluene (3,500 cc.) in the presence of p-toluenesulphonic acid monohydrate (22 g.). The mixture is heated under reflux (the water being removed at the rate of which it is formed, in a Dean and Stark apparatus) for 40 minutes, then cooled to 60° C., and concentrated to dryness under reduced pressure (20 mm.Hg). The residue is dissolved in ethyl acetate (200 cc.) and the solution is washed twice with a saturated sodium bicarbonate solution (700 cc.), and with water (twice 700 cc.) and is then dried over magnesium sulphate and finally treated with decolourising charcoal. The solution is filtered and the filtrate is concentrated to dryness under reduced pressure (20 mm.Hg). The residue obtained is dissolved hot in chloroform (450 cc.) and carbon tetrachloride (800 cc.). The mixture is cooled to 0° C., for 16 hours and the crystals obtained are filtered off. Ethyl α-hydroxyimino-(5,6-dihydro-1,4-dithiin-2-yl)-acetate (173 g.) is thus obtained in the form of white crystals melting at 142° C.

Ethyl 2-hydroxyimino-4-(2-mercapto-ethylthio)-3-oxo-butyrate can be prepared as follows:

A solution of ethyl 4-chloro-2-hydroxyimino-3-oxo-butyrate (1,050 g.) in chloroform (2,500 cc.) is added to a solution of ethanedithiol (900 cc.) and triethylamine (765 cc.) in chloroform (2,500 cc.), whilst keeping the temperature at 20° C. The mixture is left at 20° C. for 1 hour, normal hydrochloric acid (2,000 cc.) is then added and the organic phase is separated off, washed twice with water (2,000 cc.) and then dried over magnesium sulphate. After filtration, the filtrate is concentrated to dryness under reduced pressure (20 mm.Hg). Methylene chloride (500 cc.) is added to the partially crystallised residue and the mixture is then cooled to −10° C. It is then filtered and ethyl 2-hydroxyimino-4-(2-mercapto-ethylthio)-3-oxo-butyrate (655 g.) is obtained in the form of white crystals melting at 110° C.

Ethyl 4-chloro-2-hydroxyimino-3-oxo-butyrate can be prepared according to M. Hatanaka and T. Ishimaru, J. Med. Chem., 16, 978 (1973).

EXAMPLE 2

(+)-Camphorsulphonic acid (34.8 g.) is added to a suspension of DL-α-amino-(5,6-dihydro-1,4-dithiin-2-yl)-acetic acid (28.7 g.) in methanol (150 cc.). The mixture is heated gradually until it has dissolved and is then concentrated to dryness under reduced pressure (20 mm.Hg). After recrystallising the residue five times from a mixture of acetonitrile and water (90-10 by volume), the salt of (+)-camphorsulphonic acid and D-α-amino-(5,6-dihydro-1,4-dithiin-2-yl)-acetic acid (5.5 g.) is obtained in the form of white crystals.

$[\alpha]_D^{20} = -39.3° \pm 1° (c = 1, \text{water})$.

This salt (3.5 g.) is dissolved in distilled water (50 cc.) and the solution is brought to pH 4 by adding sodium bicarbonate. It is then concentrated under reduced pressure (20 mm.Hg) to a volume of 20 cc. and is left for 20 hours at 4° C. The precipitate formed is filtered off. D-α-amino-(5,6-dihydro-1,4-dithiin-2-yl)-acetic acid (1.3 g.) is thus obtained in the form of white crystals.

$[\alpha]_D^{20} = -138° \pm 1.6° (c = 1, \text{N hydrochloric acid})$.

EXAMPLE 3

Ethyl DL-α-amino-(5,6-dihydro-1,4-oxathiin-2-yl)-acetate (37 g.) is dissolved in methanol (350 cc.) and N sodium hydroxide solution (182 cc.) is then added. The reagents are left in contact for 3 hours at a temperature of about 4° C., and the solution is then concentrated under reduced pressure (20 mm.Hg) to about ⅓ of the initial volume. It is then acidified to pH 4.5, at a temperature of about 5° C, by adding 4 N hydrochloric acid. A product crystallises. The mixture is stirred for 15 minutes and the precipitate is then filtered off; DL-α-amino-(5,6-dihydro-1,4-oxathiin-2-yl)-acetic acid (19.4 g.) is thus obtained in the form of white crystals melting at about 270° C.

Ethyl DL-α-amino-(5,6-dihydro-1,4-oxathiin-2-yl)-acetate can be prepared as follows:

Ethyl α-hydroxyimino-(5,6-dihydro-1,4-oxathiin-2-yl)-acetate (295 g.) is dissolved in methanol (1.5 liters), and formic acid (1.5 liters) and water (1.5 liters) are then added. The mixture is cooled by means of a bath of ice and water and zinc powder (250 g.) is added in small portions over the course of 30 minutes. The reagents are left in contact for 2 hours whilst stirring at a temperature of about 20° C., the mixture is then filtered and the solution is concentrated under reduced pressure (20 mm.Hg) to a volume of 1 liter. Water (1.5 liters) is added and the mixture is washed twice with ethyl acetate (a total of 3 liters). The organic extracts are discarded and the aqueous phase is brought to pH 10 by adding sodium hydroxide solution and is then extracted three times with methylene chloride (a total of 1.5 liters).

The organic extracts are combined, dried over sodium sulphate, treated with decolourising charcoal, filtered and concentrated under reduced pressure (20 mm.Hg). Ethyl DL-α-amino-(5,6-dihydro-1,4-oxathiin-2-yl)-acetate (150 g.) is thus obtained in the form of an oil.

Ethyl α-hydroxyimino-(5,6-dihydro-1,4-oxathiin-2-yl)-acetate can be prepared as follows:

Ethyl 4-(2-hydroxy-ethylthio)-2-hydroxyimino-3-oxo-butyrate (321 g.) is dissolved in boiling toluene (3.2 liters) and paratoluenesulphonic acid monohydrate (26 g.) is then added. Vigorous boiling results, with liberation of water, which is removed in a DEAN and STARK apparatus. The reaction mixture is heated under reflux for a further 15 minutes. After cooling, the toluene solution is filtered, and washed three times with water (a total of 1.5 liters), then with a saturated sodium bicarbonate solution (200 cc.) and finally with water (500 cc.). It is dried over magnesium sulphate, treated with decolourising charcoal, filtered and concentrated to dryness under reduced pressure (20 mm.Hg). Ethyl α-hydroxyimino-(5,6-dihydro-1,4-oxathiin-2-yl)-acetate (273 g.) is obtained in the form of an oil which gradually solidifies.

Ethyl 4-(2-hydroxy-ethylthio)-2-hydroxyimino-3-oxo-butyrate can be prepared as follows:

Ethyl 4-chloro-2-hydroxyimino-3-oxo-butyrate (340 g.) is dissolved in chloroform (1.5 liters) and 2-mercapto-ethanol (126 cc.) is then added. Triethylamine (248 cc.) dissolved in chloroform (1 liter) is added to the resulting solution at about 20° C., over the course of 30 minutes. The reagents are left in contact for 15 hours whilst stirring at about 20° C. Then the reaction mixture is washed with water (200 cc.) followed by 2 N hydrochloric acid (200 cc.) and finally four times with water (a total of 1 liter). The organic phase is dried over sodium sulphate treated with decolourising charcoal, filtered and concentrated to dryness under reduced pressure (20 mm.Hg). Ethyl 4-(2-hydroxy-ethylthio)-2-hydroxyimino-3-oxo-butyrate (321 g.) is thus obtained in the form of an oil which gradually solidifies.

EXAMPLE 4

L-α-Amino-(5,6-dihydro-1,4-dithiin-2-yl)-acetic acid (2 g.) is prepared by enzymatic resolution of the corresponding racemate, using the following method:

a. Purification of "AMANO" acylase

The commercial enzyme, of strength about 260 U/g, and containing proteases and coloured pigments as the principal impurities, is purified by ultra-filtration through a DIAFLO XM 50 membrane in an "AMICON" cell of 15 cm. diameter, by proceeding as follows:

"AMANO" acylase (15 g.) of strength 260 U/g is dissolved in an 0.01 M tris-maleate buffer of pH 7 (400 cc.) containing $5 \times 10^{-4}$ M of $CoCl_2$. After ultra-filtration at 4° C., and lyophilisation of the retentate, a product (3.8 g.) of strength 828 U/g is obtained.

The enzyme obtained is about 3 times more active and about 7.5 times purer (in terms of the ratio acylase activity/protease activity) than the initial product.

b. Enzymatic desacetylation

DL-α-Acetamido-(5,6-dihydro-1,4-dithiin-2-yl)-acetic acid (10 g.) is dissolved in an 0.05 M sodium phosphate buffer at pH 8 (500 cc.) containing $5 \times 10^{-4}$ M of $CoCl_2$. The pH of the solution is adjusted to 8 by adding normal sodium hydroxide solution. Acylase (1.35 g.) of strength 828 U/g is then added and the total volume is made up to 2 liters by adding buffer. The desacetylation is effected by stirring the reaction mixture for 24 hours at 37° C. The complete conversion of the L-isomer to the corresponding aminoacid is ensured by adding acylase (0.3 g.) (about 250 U) whilst continuing the incubation at 37° C. for 1 hour.

The reaction mixture is cooled to 20° C., and is then ultra-filtered through an "IRIS 3042" membrane in an "AMICON" cell of 15 cm. diameter. The acylase and the impurities of molecular weight greater than 20,000 are retained in the cell. The reaction products and the salts pass into the ultrafiltrate.

The enzyme is recovered by lyophilisation of the retentate.

D-α-Acetamido-(5,6-dihydro-1,4-dithiin-2-yl)-acetic acid is precipitated from the ultra-filtrate by adding hydrochloric acid until the pH is 2. After filtration, the product is redissolved in an alkaline medium (pH = 8) and the solution is decolourised by means of "DARCO" charcoal. The purified acid is precipitated, after filtration, by adding hydrochloric acid to bring the pH to 2.

L-α-Amino-(5,6-dihydro-1,4-dithiin-2-yl)-acetic acid is isolated from the filtrates obtained above by fixation on "IR 120" resin in the acid state, at pH 2, for 15 hours, followed by elution with an ammonia solution at pH 8-9 (1,000 cc.). The filtrate is neutralised to pH 7.5 by adding hydrochloric acid and the L-α-amino-(5,6-dihydro-1,4-dithiin-2-yl)-acetic acid is precipitated by adding acetone. The precipitate is filtered and then redissolved in water at pH 6.5, and the acid is again precipitated by concentrating the solution under reduced pressure.

After filtration, L-α-amino-(5,6-dihydro-1,4-dithiin-2-yl)-acetic acid (2 g.) is thus obtained; it has the following characteristics:

Melting point = 255°-260° C., with decomposition.

$[\alpha]_D^{20} = +138° \pm 2°$ (c = 1, 1 N hydrochloric acid).

The DL-α-acetamido-(5,6-dihydro-1,4-dithiin-2-yl)-acetic acid used as the starting material can be prepared in accordance with one of the following methods:

a. Normal sodium hydroxide solution (126 cc.) is added to a solution of ethyl DL-α-acetamido-(5,6-dihydro-1,4-dithiin-2-yl)-acetate (30 g.) in ethyl alcohol (300 cc.) and the mixture is left stirring at 25° C., for 20 minutes. The solution obtained is concentrated to dryness under reduced pressure (20 mm.Hg) and the residue is taken up in water (500 cc.).

The aqueous phase is washed with ether (300 cc.) and then brought to pH 1 by adding 4 N hydrochloric acid. The suspension formed is kept in an ice bath for 30 minutes; the precipitate is filtered off and washed twice with water (50 cc.). This gives DL-α-acetamido-(5,6-dihydro-1,4-dithiin-2-yl)-acetic acid (19 g.) in the form of white crystals melting, with decomposition, at about 250° C.

Ethyl DL-α-acetamido-(5,6-dihydro-1,4-dithiin-2-yl)-acetate can be prepared as follows:

A solution of ethyl α-acetamido-γ-bromoaceto-acetate (90 g.) in chloroform (300 cc.) is added over the course of one hour and 30 minutes to a solution of ethanedithiol (63.5 g.) and triethylamine (34.2 g.) in chloroform (400 cc.) whilst keeping the temperature of the mixture at 25° C. The mixture is left stirring at 25° C. for a further hour, normal hydrochloric acid (250 cc.) is then added, the aqueous phase is separated off, and the organic phase is washed with a saturated sodium bicarbonate solution (500 cc.). The organic phase is then dried over magnesium sulphate, filtered and evaporated to dryness under reduced pressure (20 mm.Hg). Toluene (350 cc.) and p-toluenesulphonic acid monohydrate (9 g.) are added to the residue obtained and the mixture is heated under reflux for 45 minutes whilst removing the water formed by means of a Dean and Stark apparatus. The mixture is cooled and chromatographed directly on a column of alumina (1,000 g.). Elution is carried out with a mixture of ethyl acetate and cyclohexane (30–70 by volume) (6,000 cc.) to give ethyl DL-α-acetamido-(5,6-dihydro-1,4-dithiin-2-yl)-acetate (45.7 g.) as an oil.

b. Acetic anhydride (20 cc.) is added in small portions over 1 hour to a suspension of DL-α-amino-(5,6-dihydro-1,4-dithiin-2-yl)-acetic acid (5 g.) in boiling water (50 cc.). The mixture is cooled in ice and filtered through a glass frit, and the precipitate is washed with distilled water (50 cc.) and then with methanol (50 cc.). This gives DL-α-acetamido-(5,6-dihydro-1,4-dithiin-2-yl)-acetic acid (5.4 g.) in the form of white crystals melting, with decomposition, at about 250° C.

The following Examples show how the compounds according to the present invention can be used as starting materials for the preparation of the cephalosporins of formula (X).

EXAMPLE A

Preparation of 3-acetoxymethyl-7-[DL-α-amino-(5,6-dihydro-1,4-dithiin-2-yl)-acetamido]-2-carboxy-8-oxo-5-thia-1-aza-bicyclo[4.2.0]oct-2-ene trifluoroacetate.

Tert.-butoxycarbonyl azide (14.3 g.) is added to a suspension of DL-α-amino-(5,6-dihydro-1,4-dithiin-2-yl)-acetic acid (9.55 g.) in dimethylformamide (150 cc.) and triethlyamine (17.6 cc.). This suspension is stirred at 35° C for 3 days. The reaction mixture has at that stage become homogeneous. Water (1,000 cc.) and a saturated sodium bicarbonate solution (100 cc.) are added thereto and the mixture is washed twice with ethyl ether (300 cc.). The aqueous phase is brought to pH 3 by adding citric acid. The precipitate formed is filtered off, washed with water and recrystallised from acetonitrile (400 cc.). This gives DL-α-tert.-butoxycarbonylamino-(5,6-dihydro-1,4-dithiin-2-yl)-acetic acid (12 g.) in the form of white crystals melting at about 205° C, with decomposition.

Tert.-butoxycarbonyl azide can be prepared according to L. A. CARPINO, B. A. CARPINO, P. J. CROWLEY, C. A. GIZA and P. H. TERRY, Org. Synth., 44, 15 (1964).

Dicyclohexylcarbodiimide (9.20 g.) is added to a solution of DL-α-tert.-butoxycarbonylamino-(5,6-dihydro-1,4-dithiin-2-yl)-acetic acid (11.5 g.) and 3-acetoxy-7-amino-2-tert.-butoxycarbonyl-8-oxo-5-thia-1-azabicyclo-[4.2.0]oct-2-ene (12.9 g.) in anhydrous dimethylformamide (100 cc.). The reaction mixture is stirred for 30 minutes at a temperature of about 20° C, the precipitate is then filtered off, ethyl acetate (300 cc.) is added to the filtrate and the organic phase is washed twice with water (1,000 cc.), with a 1% citric acid solution (500 cc.), then with a saturated sodium bicarbonate solution (300 cc.) and finally with water (500 cc.). The organic phase is dried over magnesium sulphate, treated with decolourising charcoal, filtered and concentrated to dryness under reduced pressure (20 mm Hg). A residue (26 g.) is obtained, which is chromatorgraphed on silica gel (300 g.). 3-Acetoxy-methyl-7-[DL-α-tert.-butoxycarbonylamino-(5,6-dihydro-1,4-dithiin-2-yl)-acetamido]-2-tert.-butoxycarbonyl-8-oxo-5-thia-1-azabicyclo[4.2.0]oct-2-ene (19 g.) is obtained after elution with a mixture of ethyl acetate and cyclohexane (35–65 by volume) (2,000 cc.) and concentration by removal of the solvent.

This product (19 g.) is dissolved in trifluoroacetic acid (100 cc.) and the solution is left for 15 minutes at a temperature of about 20° C; the trifluoroacetic acid is then driven off under reduced pressure (1 mm Hg). The residue is dissolved in ethyl acetate (75 cc.) and isopropyl ether (100 cc.) is then added. A precipitate appears, which is filtered off. 3-Acetoxymethyl-7-[DL-α-amino-(5,6-dihydro-1,4-dithiin-2-yl)-acetamido]-2-carboxy-8-oxo-5-thia-1-aza-bicyclo[4.2.0.]oct-2-ene trifluoroacetate (14.6 g.) is thus obtained in the form of a cream-coloured solid.

$[\alpha]_D^{20} = +29.2° \pm 0.9°$ ($c = 1$, dimethylformamide).

3-Acetoxymethyl-7-amino-2-tert.-butoxycarbonyl-8-oxo-5-thia-1-aza-bicyclo[4.2.0]oct-2-ene can be prepared according to R. J. STEDMAN, J. MED. Chem., 9, 444, (1966).

EXAMPLE B

Preparation of 7-[DL-α-amino-(5,6-dihydro-1,4-dithiin-2-yl)-acetamido]-2-carboxy-3-methyl-8-oxo-5-thia-1-aza-bicyclo[4.2.0]oct-2-ene trifluoroacetate.

Dicyclohexylcarbodiimide (6.2 g.) is added to a solution of DL-α-tert.-butoxycarbonylamino-(5,6-dihydro-1,4-dithiin-2-yl)-acetic acid (8.15 g.) and 7-amino-3-methyl-8-oxo-2-(2,2,2-trichloro-ethoxycarbonyl)-5-thia-1-aza-bicyclo[4.2.0]oct-2-ene (9.55 g.) in dimethyl-formamide (120 cc.), and the mixture is left stirring for 2 hours. The mixture is then filtered and the filtrate is diluted with ethyl acetate (150 cc.) and washed with water (600 cc.), 4 N hydrochloric acid (250 cc.), sodium bicarbonate (250 cc.) and distilled water (250 cc.). The organic phase is dried over magnesium sulphate, treated with decolourising charcoal, filtered and concentrated to dryness under reduced pressure (20 mm Hg). This gives a residue (17.4 g.) which is chromatographed on silica gel (250 g.) 7-[DL-α-tert.-butoxycarbonylamino-(5,6-dihydro-1,4-dithiin-2-yl)-acetamido]-3-methyl-8-oxo-2-(2,2,2-trichloro-ethoxycarbonyl)-5-thia-1-aza-bicyclo-[4.2.0]oct-2-ene (11.8 g.), in the form of a pale yellow varnish, is eluted with a mixture of ethyl acetate and cyclohexane (30-70 by volume) (2,000 cc.).

Zinc powder (11.1 g.) is added to a solution of 7-[DL-α-tert.-butoxycarbonylamino-(5,6-dihydro-1,4-dithiin-2-yl)-acetamido]-3-methyl-8-oxo-2-(2,2,2-trichloroethoxycarbonyl)-5-thia-1-aza-bicyclo[4.2.0]oct-2-ene (11.8 g.) in a mixture of dimethylformamide (60 cc.) and glacial acetic acid (30 cc.) cooled in an ice bath, and the mixture is stirred for 3 hours. The reaction mixture is then filtered; ethyl acetate (200 cc.) is added to the filtrate, which is then washed with water (500 cc.). The aqueous phase is extracted with ethyl acetate (200 cc.); the organic phases are combined, washed with water (200 cc.) and then extracted twice with a saturated sodium bicarbonate solution (200 cc.). The alkaline solution is acidified to pH 2.5 by adding 4 N hydrochloric acid in the presence of ethyl acetate (200 cc.) and the organic fraction is washed with water (200 cc.), dried over magnesium sulphate, treated with decolourising charcoal and filtered. The filtrate is concentrated to dryness under reduced pressure (20 mm Hg). 7-[DL-α-Tert.-butoxycarbonylamino-(5,6-dihydro-1,4-dithiin-2-yl)-acetamido]-2-carboxy-3-methyl-8-oxo-5-thia-1-aza-bicyclo[4.2.0]oct-2-ene (8.5 g.) is thus obtained in the form of a colourless varnish.

7-[DL-α-Tert.-butoxycarbonylamino-(5,6-dihydro-1,4-dithiin-2-yl)-acetamido]-2-carboxy-3-methyl-8-oxo-5-thia-1-aza-bicyclo[4.2.0]oct-2-ene (8.5 g.) is dissolved in trifluoroacetic acid (80 cc.). The solution obtained is left to stand for 10 minutes and the trifluoroacetic acid is then driven off under reduced pressure (1 mm Hg). The residue obtained is dissolved in ethyl acetate (10 cc.) and ethyl ether (120 cc.) is added. A product precipitates, which is filtered off. 7-[DL-α-Amino-(5,6-dihydro-1,4-dithiin-2-yl)-acetamido]-2-carboxy-3-methyl-8-oxo-5-thia-1-aza-bicyclo[4.2.0]oct-2-ene trifluoroacetate (6.8 g.) is thus obtained in the form of a white powder.

$[\alpha]_D^{20} = + 88.6° \pm 1.4°$ ($c = 1$, dimethylformamide).

7-Amino-3-methyl-8-oxo-2-(2,2,2-trichloroethoxycarbonyl)-5-thia-1-aza-bicyclo[4.2.0]oct-2-ene can be prepared according to R. R. CHAUVETTE, P. A. PENNINGTON, C. W. RYAN, R. D. G. COOPER, F. L. JOSE, I. G. WRIGHT, E. M. VAN HEYNINGEN and G. W. HUFFMAN, J. Org. Chem. 36, 1259 (1971).

EXAMPLE C

Preparation of 7-[D-α-amino-(5,6-dihydro-1,4-dithiin-2-yl)-acetamido]-2-carboxy-3-methyl-8-oxo-5-thia-1-aza-bicyclo[4.2.0]oct-2-ene trifluoroacetate.

Following the procedure in Example A, D-α-tert.-butoxycarbonylamino-(5,6-dihydro-1,4-dithiin-2-yl)-acetic acid (5.4 g.) $[\alpha]_D^{20} = - 109° \pm 2°$ ($c = 1$, dimethyl-formamide), is obtained by reaction of tert.-butoxycarbonyl azide (8.6 g.) with D-α-amino-(5,6-dihydro-1,4-dithiin-2-yl)-acetic acid (5.5 g.) in dimethylformamide (100 cc.) containing triethylamine (10.5 cc.).

On following the procedure in Example B but starting from D-α-tert.-butoxycarbonylamino-(5,6-dihydro-1,4-dithiin-2-yl)-acetic acid (5.2 g.) and 7-amino-3-methyl-8-oxo-2-(2,2,2-trichloro-ethoxycarbonyl)-5-thia-1-aza-bicyclo[4.2.0]oct-2-ene (6.1 g.) in dimethylformamide (120 cc.) in the presence of dicyclohexylcarbodiimide (4.02 g.), 7-[D-α-tert.-butoxycarbonylamino-(5,6-dihydro-1,4-dithiin-2-yl)-acetamido]-3-methyl-8-oxo-2-(2,2,2-trichloro-ethoxycarbonyl)-5-thia-1-aza-bicyclo[4.2.0]oct-2-ene (5.2 g.) is obtained.

$[\alpha]_D^{20} = +45.6° \pm 1°$ ($c = 1$, chloroform).

On treating 7-[D-α-tert.-butoxycarbonylamino-(5,6-dihydro-1,4-dithiin-2-yl)-acetamido]-3-methyl-8-oxo-2-(2,2,2-trichloro-ethoxycarbonyl)-5-thia-1-aza-bicyclo-[4.2.0]oct-2-ene (5.2 g.) with zinc powder (5.05 g.) in dimethylformamide (30 cc.) and glacial acetic acid (15 cc.), 7-[D-α-tert.-butoxycarbonylamino-(5,6-dihydro-1,4-dithiin-2-yl)-acetamido]-2-carboxy-3-methyl-8-oxo-5-thia-1-aza-bicyclo[4.2.0]oct-2-ene (3.8 g.) is obtained in the form of a colourless varnish.

7-[D-α-Tert.-butoxycarbonylamino-(5,6-dihydro-1,4-dithiin-2-yl)-acetamido]-2-carboxy-3-methyl-8-oxo-5-thia-1-aza-bicyclo[4.2.0]oct-2-ene (3.7 g.) is dissolved in trifluoroacetic acid (35 cc.) and this solution is left stirring for 10 minutes at about 20° C. The mixture is concentrated to dryness under reduced pressure (1 mm Hg), the residue is dissolved in ethyl acetate (6 cc.) and ethyl ether (70 cc.) is added. A precipitate forms, and is filtered off. 7-[D-α-Amino-(5,6-dihydro-1,4-dithiin-2-yl)-acetamido]-2-carboxy-3-methyl-8-oxo-5-thia-1-aza-bicyclo[4.2.0]oct-2-ene (1.8 g.) is thus obtained in the form of a white powder.

$[\alpha]_D^{20} = + 119.2° \pm 1.8°$ ($c = 1$, dimethylformamide).

EXAMPLE D

Preparation of 7-[DL-α-amino(5,6-dihydro-1,4-oxathiin-2-yl)-acetamido]-2-carboxy-3-methyl-8-oxo-5-thia-1-aza-bicyclo[4.2.0]oct-2-ene trifluoroacetate.

DL-α-Amino-(5,6-dihydro-1,4-oxathiin-2-yl)-acetic acid (25.4 g.) is suspended in dimethylformamide (435 cc.); tert.-butoxycarbonyl azide (41.5 g.) and triethylamine (51 cc.) are added. The reagents are left in contact for 48 hours whilst stirring at a temperature of 35° C. The solution is concentrated under reduced pressure (1 mm Hg), the residue is taken up in water (300 cc.), and the pH is adjusted to 8.5 by adding a saturated sodium bicarbonate solution. The aqueous phase is extracted twice with ethyl ether (a total of 500 cc.) which is discarded, and is then acidified to pH = 3 by adding 4 N hydrochloric acid A product precipitates, which is filtered off and then dissolved in methylene chloride (600 cc.). The solution obtained is dried over magnesium sulphate, filtered and concentrated to dryness under reduced pressure (20 mm Hg). DL-α-Tert.-butoxycarbonylamino-(5,6-dihydro-1,4-oxathiin-2-yl)-acetic acid (26.2 g.), melting at 160° C is thus obtained.

7-Amino-3-methyl-8-oxo-2-(2,2,2-trichloroethoxycarbonyl)-5-thia-1-aza-bicyclo[4.2.0]oct-2-ene (17.6 g.) and dicyclohexylcarbodiimide (11.5 g.) are added to a solution of DL-α-tert.-butoxycarbonylamino-(5,6-dihydro-1,4-oxathiin-2-yl)-acetic acid (14 g.) in chloroform (120 cc.) and the mixture is left stirring for 12 hours at a temperature of about 20° C. The reaction mixture is filtered and the filtrate is concentrated under reduced pressure (20 mm Hg). A gummy residue is obtained, which is dissolved in ethyl acetate (250 cc.); the solution is washed twice with 2 N hydrochloric acid (a total of 200 cc.), then twice with a saturated sodium bicarbonate solution (a total of 200 cc.) and finally twice with water (a total of 200 cc.). The organic phase is dried over magnesium sulphate, treated with decolourising charcoal, filtered and then concentrated under reduced pressure (20 mm Hg). A residue (35 g.) is obtained, which is chromatographed on silica (350 g.).

Elution is carried out successively with a 1:9 by volume mixture of ethyl acetate and cyclohexane (400 cc.) and then with a 15:85 by volume mixture of ethyl acetate and cyclohexane (800 cc.). The corresponding eluates are discarded. Elution is then again carried out with a 15:85 by volume mixture of ethyl acetate and cyclohexane (1,400 cc.).

The eluate thus obtained is concentrated to dryness under reduced pressure (20 mm Hg). 3-Methyl-8-oxo-7-[DL-α-tert.-butoxycarbonylamino-(5,6-dihydro-1,4-oxathiin-2-yl)-acetamido]-2-(2,2,2-trichloroethoxycarbonyl)-5-thia-1-aza-bicyclo[4.2.0]oct-2-ene (23.5 g.) is thus obtained in the form of an amorphous white powder.

3-Methyl-8-oxo-7-[DL-α-tert.-butoxycarbonylamino-(5,6-dihydro-1,4-oxathiin-2-yl)-acetamido]-2-(2,2,2-trichloro-ethoxycarbonyl)-5-thia-1-aza-bicyclo[4.2.0]oct-2-ene (23.4 g.) is dissolved in dimethylformamide (135 cc.) and acetic acid (40 cc.). Zinc powder (22 g.) is added to this solution and the mixture is stirred for 3 hours at about 20° C. It is filtered through Supercel and the solution is then concentrated under reduced pressure (0.1 mm Hg). An oil is obtained, which is taken up in water (800 cc.) and extracted twice with ethyl acetate (a total of 400 cc.). The organic phase is treated twice with a saturated sodium bicarbonate solution (a total of 400 cc.) and the aqueous fraction is acidified, in the presence of ethyl acetate (200 cc.) by adding 4 N hydrochloric acid until the pH is 2.5. The organic phase is decanted, washed with water (100 cc.), dried over magnesium sulphate, treated with decolourising charcoal, filtered and concentrated under reduced pressure (20 mm Hg). 2-Carboxy-3-methyl-8-oxo-7-[DL-α-tert.-butoxycarbonylamino-(5,6-dihydro-1,4-oxathiin-2-yl)-acetamido]-5-thia-1-aza-bicyclo[4.2.0]oct-2-ene (13.9 g.) is obtained in the form of an amorphous white powder.

2-Carboxy-3-methyl-8-oxo-7-[DL-α-tert.-butoxy-carbonylamino-(5,6-dihydro-1,4-oxthiin-2-yl)-acetamido]-5-thia-1-aza-bicyclo[4.2.0]oct-2-ene (13.8 g.) is dissolved in trifluoroacetic acid (139 cc.). The reagents are left in contact for 15 minutes, whilst stirring, at a temperature of about 0° C. The mixture is then concentrated to dryness under reduced pressure (1 mm Hg), the residue is taken up in ethyl acetate (100 cc.) and the solution is again concentrated to dryness under reduced pressure (1 mm Hg). The residue obtained is dissolved in ethyl acetate (100 cc.) and this solution is then poured into ethyl ether (300 cc.); a product precipitates. The precipitate is washed twice by decantation with ethyl ether (a total of 600 cc.) and is then isolated by filtration. 7-[DL-α-Amino-(5,6-dihydro-1,4-oxathiin-2-yl)-acetamido]-2-carboxy-3-methyl-8-oxo-5-thia-1-aza-bicyclo[4.2.0]oct-2-ene trifluoroacetate (11.4 g.) is thus obtained.

$[\alpha]_D^{20} = +114.2° \pm 1.7°$ ($c = 1.3$, dimethylformamide).

EXAMPLE E

Preparation of 3-acetoxymethyl-7-[DL-α-amino-(5,6-dihydro-1,4-oxathiin-2-yl)-acetamido]-2-carboxy-8-oxo-5-thia-1-aza-bicyclo[4.2.0]oct-2-ene trifluoroacetate.

3-Acetoxymethyl-7-amino-8-oxo-2-tert.-butoxycarbonyl-5-thia-1-aza-bicyclo[4.2.0]oct-2-ene (11.2 g.) and dicyclohexylcarbodiimide (7.7 g.) are added to a solution of DL-α-tert.-butoxycarbonylamino-(5,6-dihydro-1,4-oxathiin-2-yl)-acetic acid (9.4 g.) in chloroform (85 cc.). The reagents are left in contact for 12 hours whilst stirring at a temperature of about 20° C and the solid formed is then filtered off. The filtrate is concentrated under reduced pressure (20 mm Hg) and the residue is dissolved in ethyl acetate (200 cc.). The solution is washed twice with 2 N hydrochloric acid (a total of 150 cc.), then twice with a saturated sodium bicarbonate solution (a total of 150 cc.) and finally twice with water (a total of 200 cc.). The organic phase is dried over sodium sulphate, treated with decolourising charcoal, filtered and then concentrated under reduced pressure (20 mm Hg). A residue (25 g.) is obtained, which is chromatographed on silica (250 g.). Elution is carried out successively with a 1:9 by volume mixture of ethyl acetate and cyclohexane (120 cc.) and then with a 15:85 by volume mixture of ethyl acetate and cyclohexane (360 cc.). The corresponding eluates are discarded. Elution is then carried out with a 35:65 by volume mixture of ethyl acetate and cyclohexane (360 cc.). The eluate thus obtained is concentrated to dryness under reduced pressure (20 mm Hg). 3-Acetoxymethyl-8-oxo-7-[DL-α-tert.-butoxycarbonylamino-(5,6-dihydro-1,4-oxathiin-2-yl)-acetamido]-2-tert.-butoxycarbonyl-5-thia-1-aza-bicyclo[4.2.0]oct-2-ene (12.8 g.) is thus obtained in the form of an amorphous white powder.

3-Acetoxymethyl-8-oxo-7-[DL-α-tert.-butoxycarbonylamino-(5,6-dihydro-1,4-oxathiin-2-yl)-acetamido]-2-tert.-butoxycarbonyl-5-thia-1-aza-bicyclo[4.2.0]oct-2-ene (12.7 g.) is dissolved in trifluoroacetic acid (120 cc.). The reagents are left in contact for 15 minutes whilst stirring at a temperature of about 20° C. The mixture is then concentrated to dryness under reduced pressure (1 mm Hg), the residue is taken up in ethyl acetate (100 cc.) and the solution is again concentrated to dryness under reduced pressure (1 mm Hg). The residue obtained is dissolved in ethyl acetate (25 cc.) and this solution is then poured into ethyl ether (100 cc.); a product precipitates. The precipitate is washed twice by decantation with ethyl ether (a total of 500 cc.) and is then filtered off. 3-Acetoxymethyl-7-[DL-α-amino-(5,6-dihydro-1,4-oxathiin-2-yl)-acetamido]-2-carboxy-8-oxo-5-thia-1-aza-bicyclo[4.2.0]oct-2-ene trifluoroacetate (9.7. g.) is thus obtained. $[\alpha]_D^{20} = +24.0° \pm 0.8°$ ($c = 1$, dimethylformamide).

We claim:

1. An oxathiino- or dithiino-aminoacetic acid of formula:

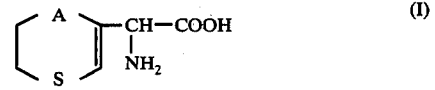

in which A is oxygen or sulphur, in racemic or optically active form, as the free acid or as a derivative thereof selected from an acid addition salt, an acid halide, and the anhydride.

2. A compound according to claim 1 which is DL-α-amino-(5,6-dihydro-1,4-dithiin-2-yl)-acetic acid.

3. A compound according to claim 1 which is D-α-amino-(5,6-dihydro-1,4-dithiin-2-yl)-acetic acid.

4. A compound according to claim 1 which is DL-α-amino-(5,6-dihydro-1,4-oxathiin-2-yl)-acetic acid.

5. A compound according to claim 1 which is L-α-amino-(5,6-dihydro-1,4-dithiin-2-yl)acetic acid.

* * * * *